(12) United States Patent
Dishler et al.

(10) Patent No.: US 11,272,986 B2
(45) Date of Patent: Mar. 15, 2022

(54) DEVICE FOR SURGICALLY CORRECTING AMETROPIA OF AN EYE AND METHOD FOR CREATING CONTROL DATA THEREFOR

(71) Applicant: Carl Zeiss Meditec AG, Jena (DE)

(72) Inventors: Jon Dishler, Greenwood Village, CO (US); Mark Bischoff, Jena (DE); Gregor Stobrawa, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 60 days.

(21) Appl. No.: 16/322,352

(22) PCT Filed: Aug. 1, 2017

(86) PCT No.: PCT/EP2017/069426
§ 371 (c)(1),
(2) Date: Jan. 31, 2019

(87) PCT Pub. No.: WO2018/024721
PCT Pub. Date: Feb. 8, 2018

(65) Prior Publication Data
US 2019/0175281 A1 Jun. 13, 2019

Related U.S. Application Data

(60) Provisional application No. 62/369,512, filed on Aug. 1, 2016.

(51) Int. Cl.
*A61F 9/008* (2006.01)
*A61B 34/10* (2016.01)
*A61B 18/00* (2006.01)

(52) U.S. Cl.
CPC .......... *A61B 34/10* (2016.02); *A61F 9/00829* (2013.01); *A61F 9/00836* (2013.01);
(Continued)

(58) Field of Classification Search
None
See application file for complete search history.

(56) References Cited

U.S. PATENT DOCUMENTS

| 5,549,632 A | 8/1996 | Lai |
| 56,556,186 | 8/1997 | Mourou et al. |

(Continued)

FOREIGN PATENT DOCUMENTS

| DE | 69500997 T2 | 4/1998 |
| DE | 10334110 A1 | 2/2005 |

(Continued)

OTHER PUBLICATIONS

U.S. Appl. No. 56/556,186, filed Aug. 1997, Mourou et al.
(Continued)

*Primary Examiner* — Lynsey C Eiseman
(74) *Attorney, Agent, or Firm* — Patterson Thuente Pedersen, P.A.

(57) ABSTRACT

A device and a method for producing control data, which are designed to control a laser machining device to surgically correct ametropia of an eye in which, in order to define a space in the cornea, defines a front cutting surface, a rear cutting surface and an edge section, which are to be produced as cutting surfaces in the cornea. The rear cutting surface has a non-circular, oval edge lying in a plane, the edge section connecting the edge to the front cutting surface and the edge section being designed as a non-rotationally symmetrical cylinder or truncated cone, the base of which is the edge.

7 Claims, 11 Drawing Sheets

(52) U.S. Cl.
CPC . *A61B 2018/00696* (2013.01); *A61F 9/00838* (2013.01); *A61F 2009/00872* (2013.01); *A61F 2009/00882* (2013.01); *A61F 2009/00897* (2013.01)

(56) References Cited

U.S. PATENT DOCUMENTS

| | | | |
|---|---|---|---|
| 5,993,438 | A | 11/1999 | Juhasz |
| 6,090,100 | A | 7/2000 | Hohl |
| 6,110,166 | A | 8/2000 | Juhasz |
| 6,467,907 | B1 | 10/2002 | Fujieda et al. |
| 7,131,968 | B2 | 11/2006 | Bendett et al. |
| 2001/0010003 | A1 | 7/2001 | Lai |
| 2004/0070761 | A1 | 4/2004 | Horvath et al. |
| 2005/0195364 | A1 | 9/2005 | Dai |
| 2007/0293851 | A1 | 12/2007 | Muhlhoff et al. |
| 2008/0319428 | A1* | 12/2008 | Wiechmann ........ A61F 9/00829 606/5 |
| 2010/0087802 | A1* | 4/2010 | Bischoff .................. A61F 2/142 606/4 |
| 2010/0331830 | A1 | 12/2010 | Bischoff et al. |
| 2010/0331831 | A1 | 12/2010 | Bischoff et al. |
| 2012/0016351 | A1 | 1/2012 | Stobrawa et al. |
| 2014/0288540 | A1 | 9/2014 | Bischoff et al. |

FOREIGN PATENT DOCUMENTS

| | | |
|---|---|---|
| DE | 102006053117 A1 | 5/2008 |
| DE | 102006053118 A1 | 5/2008 |
| DE | 102006053119 A1 | 5/2008 |
| DE | 102006053120 A1 | 5/2008 |
| DE | 102007053281 A1 | 5/2009 |
| DE | 102007053283 A1 | 5/2009 |
| DE | 102012018421 A1 | 3/2014 |
| EP | 1153584 A1 | 11/2001 |
| EP | 1159986 A2 | 12/2001 |
| EP | 3 03 7077 A1 | 6/2016 |
| WO | WO 96/11655 A1 | 4/1996 |
| WO | WO 2004/032810 A2 | 4/2004 |
| WO | WO 2005/092172 A1 | 10/2005 |
| WO | WO 2010/084162 A2 | 7/2010 |

OTHER PUBLICATIONS

PCT International Preliminary Report on Patentability for International Application No. PCT/EP2017/069426, dated Feb. 14, 2019, 15 pages.
International Search Report for International Application No. PCT/EP2017/069426, dated Nov. 13, 2017; 4 pages.
English translation of International Search Report for International Application No. PCT/EP2017/069426, dated Nov. 13, 2017; 2 pages.
Written Opinion of the ISA for International Application No. PCT/EP2017/069426, dated Nov. 13, 2017; 6 pages.
Bronstein I., Taschenbuch der Mathematik, Teubner Verlag, 22nd edition, 1985, Section 2.6.2.4, 2 pages.

* cited by examiner

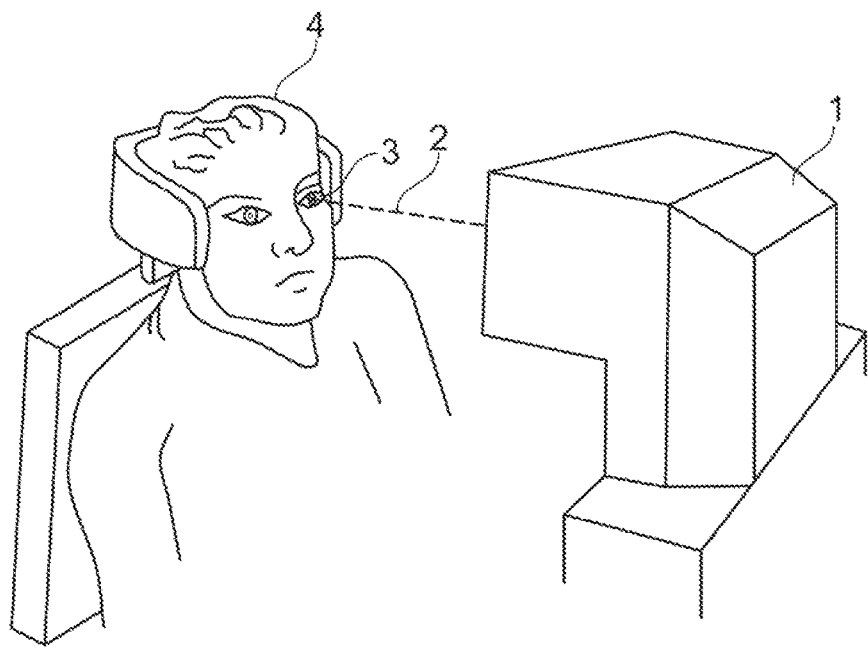
Fig. 1
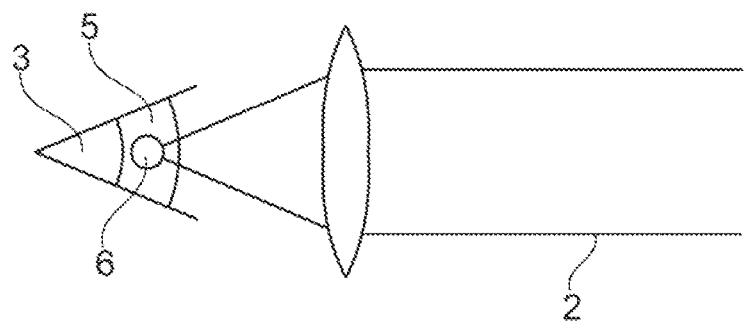
Fig. 3
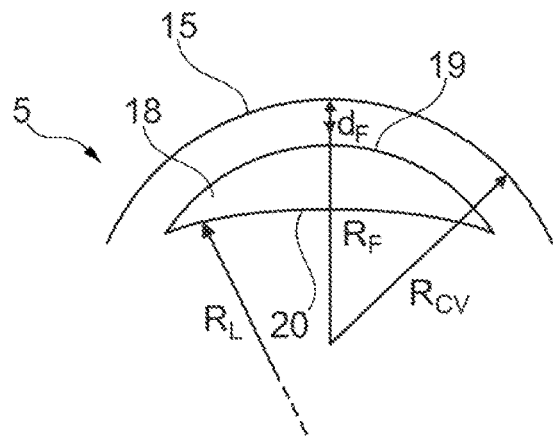 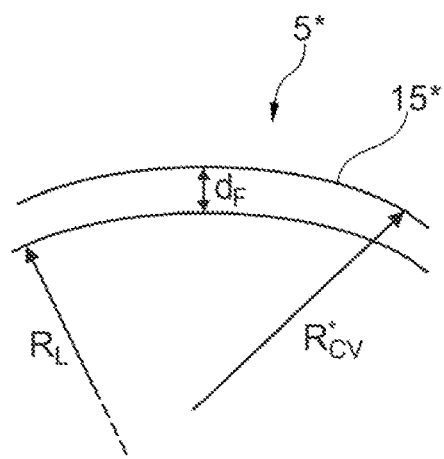
Fig. 5        Fig. 6

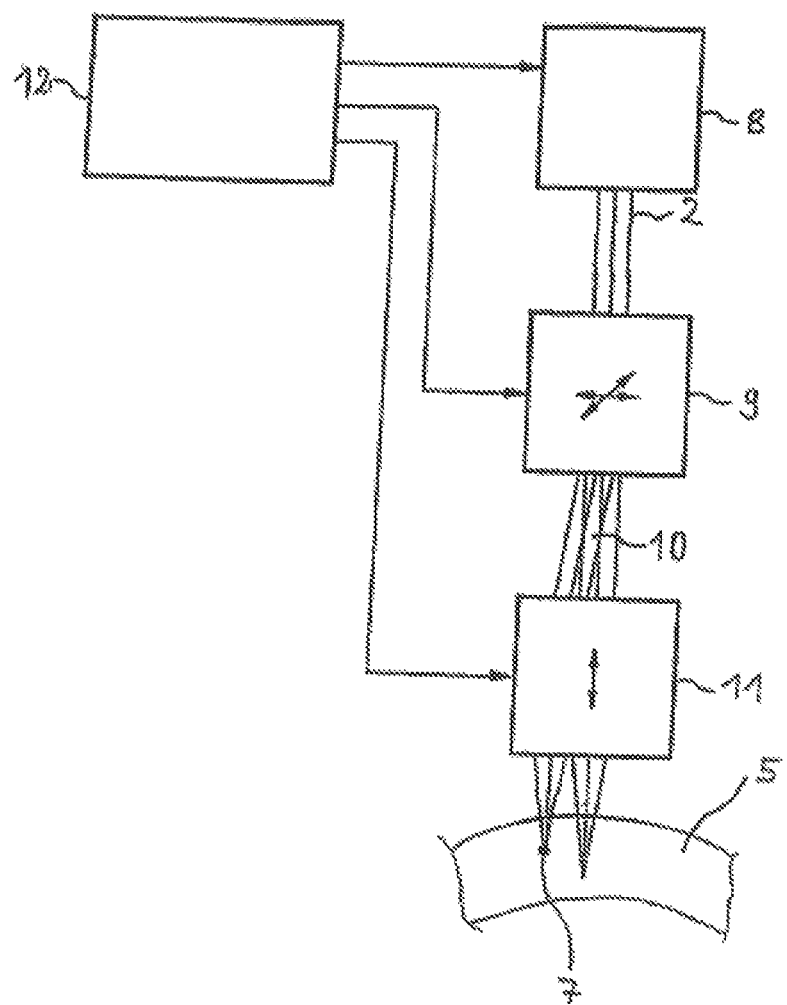
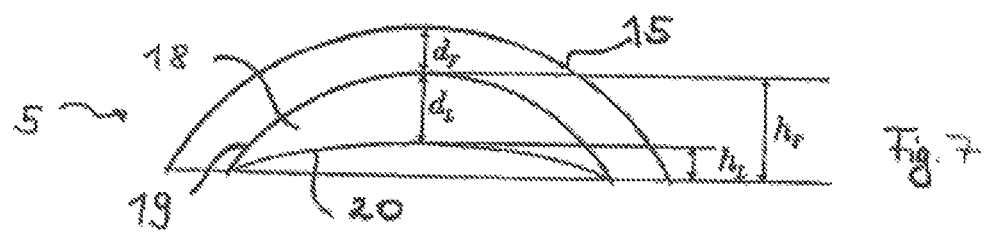

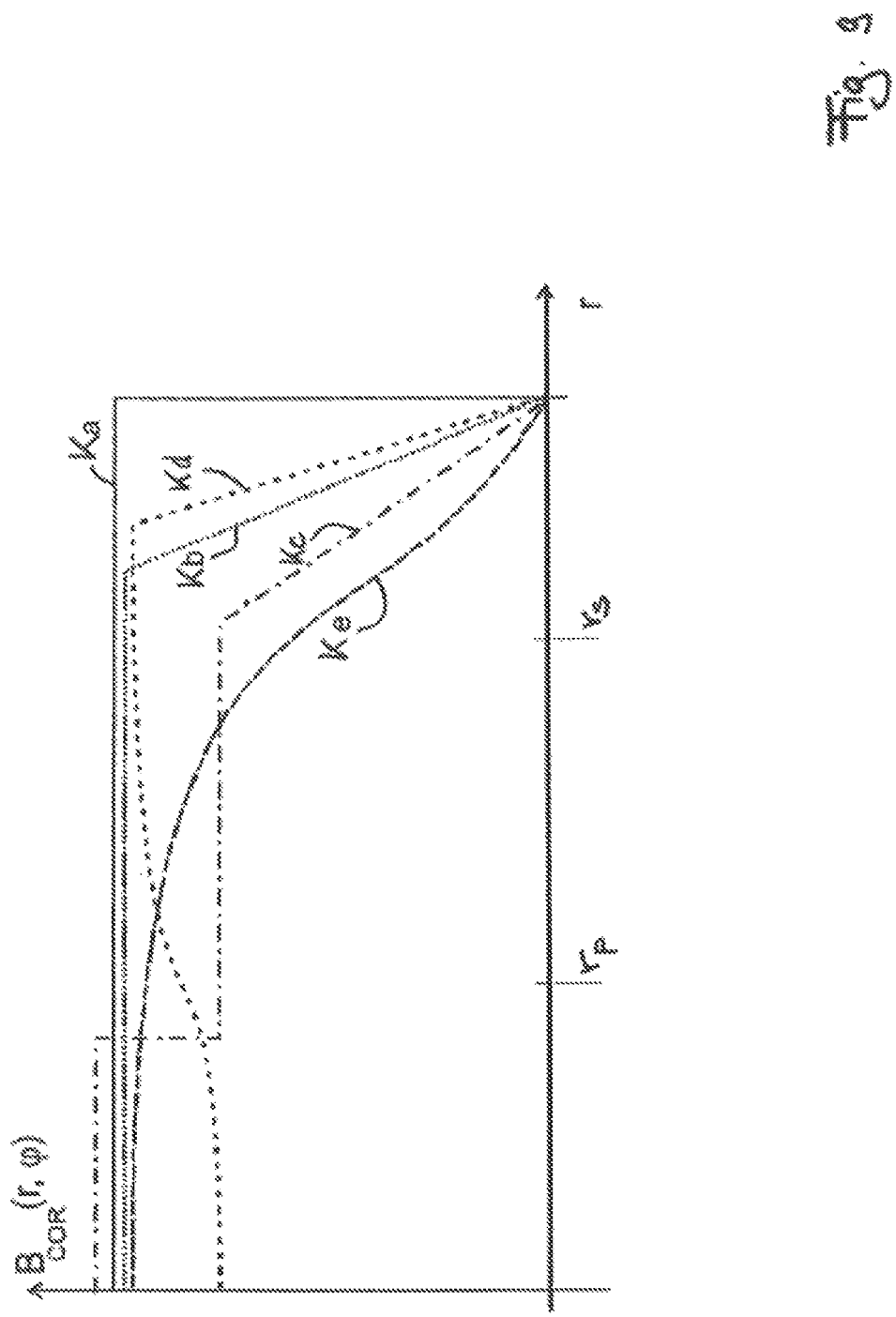

DEVICE FOR SURGICALLY CORRECTING AMETROPIA OF AN EYE AND METHOD FOR CREATING CONTROL DATA THEREFOR

RELATED APPLICATIONS

This application is a National Phase entry of PCT Application No. PCT/EP2017/069426 filed Aug. 1, 2017, which application claims the benefit of priority to U.S. Application No. 62/369,512, filed Aug. 1, 2016, the entire disclosures of which are incorporated herein by reference.

FIELD OF THE INVENTION

The invention relates to an apparatus for correcting the refractive error of an eye by surgery and a method for producing control data for controlling the apparatus, wherein the control data define an anterior surface, a posterior surface and a side cut in the cornea for enclosing a volume in the cornea. The invention further relates to a method for correcting the refractive error of an eye of a patient by surgery, wherein a volume is isolated in the cornea by virtue of an anterior surface, a posterior surface and a side cut in the cornea and which enclose the volume, being defined.

BACKGROUND

Spectacles are a conventional way of correcting the refractive error of the human eye. However, refractive surgery has found increased use in recent times, said surgery bringing about a correction of the refractive error by changing the cornea of the eye. Here, the goal of the surgical methods is to modify the cornea in a targeted fashion in order thus to influence the refraction of light. Different surgical methods are known to this end. Currently, the most widespread of these is the so-called laser in-situ keratomileusis, which is also abbreviated LASIK. In the process, a corneal lamella is initially detached from the corneal surface on one side and folded to the side. This lamella can be detached by application of a mechanical microkeratome, or else by use of a so-called laser keratome, as distributed by Abbott Medical Optics Inc., Santa Ana, USA, for example. Once the lamella has been detached and folded to one side, the application of an excimer laser is provided in the LASIK operation, said laser removing the corneal tissue exposed in this way by ablation. After a volume lying in the cornea was evaporated in this manner, the corneal lamella is folded back onto its original location again.

Applying a laser keratome for exposing the lamella is advantageous as this reduces the risk of infection and increases the cut quality. In particular, the lamella can be produced with a much more constant thickness. Additionally, the cut is potentially smoother, reducing subsequent optical disturbances by this boundary that still remains after the operation. For the purposes of producing a cut, a series of optical perforations is produced at predetermined locations in such a way that this forms the cut surface. In the case of the laser keratome, the cut surface forms the lamella that should be folded away before the use of the laser ablation.

In the conventional LASIK method, exposed corneal tissue is evaporated, which is also referred to as "polishing" the cornea by application of laser radiation. In this case, the removal of the volume, which is necessary for correcting the refractive error, is set for each surface element of the exposed cornea by way of the number of laser pulses and the energy thereof. Therefore, a so-called shot file is provided for the ablation laser within the scope of the LASIK method, said shot file, for various points on the cornea of the eye, defining how often the laser beam should be directed to defined points on the cornea and the intended energy thereof. Here, the removal of volume was established heuristically, not least as it depends very strongly on the ablation effect of the laser beam, and consequently on the wavelength, fluence, etc. of the employed radiation. Additionally, the state of the cornea of the eye also plays a role; in particular, the moisture content of the cornea of the eye should be mentioned in this respect. WO 96/11655 presents an apparatus and a method for the LASIK method. There, in particular, a formula is specified, which calculates the corneal radius of curvature to be obtained from the preoperative corneal radius of curvature and the desired diopter correction. A similar calculation is described in EP 1153584 A1 —likewise for corneal ablation by means of LASIK.

U.S. Pat. No. 5,993,438 proposes the removal of a volume from the cornea by evaporation and absorption in the cornea.

WO 2005/092172 discloses how refractive power measurements that were established in one plane can be transformed into another plane. The document mentions that this procedure can be used for various eye treatments, in particular for the laser-assisted ablation.

A further laser-based, ophthalmic surgical method consists of not evaporating the corneal volume to be removed but of isolating it by a laser cut. Thus, the volume is no longer ablated but isolated in the cornea by way of a three-dimensional cut surface, and hence made removable. Empirical values that were developed for polishing the cornea by application of ablation laser radiation are not usable for such methods. Instead, control data are required for the operation of the laser for isolating the corneal volume to be removed. U.S. Pat. Nos. 6,110,166 and 7,131,968 B2 have described such an ophthalmic surgical method. Here, U.S. Pat. No. 6,110,166 has shown various volume forms and it mentions that a person skilled in the art is able to select the fitting volume.

DE 102006053118 A1 describes the production of control data for the volume-isolating refractive error correction. DE 102006053117 A1 likewise discusses the production of control data for the volume-isolating refractive error correction. Inter alia, these disclose trajectories for shifting a focal spot of laser radiation, which form an elliptic spiral in a plan view.

DE 102006053120 A1 and DE 102006053119 A1 by Carl Zeiss Meditec AG have disclosed proceeding from refractive error data that specify the refractive power of spectacles suitable for the refractive error correction when producing such control data. This document, which consequently presents a method and an apparatus, also has disclosed the use of data that bring about an astigmatism correction or corrections of higher-order aberrations. The approach known from DE 102006053120 A1 achieves a significant simplification in the preoperative eye measurement by using refractive error data envisaged for conventional spectacles correction since the production of spectacles correction data is daily routine in ophthalmology. However, this simplification is also accompanied by a certain restriction in the possible correction results because, necessarily, only corrections that would be possible with normal spectacles can be achieved. What should also be noted in this case is that corrections as are possible with varifocal spectacles, for example, do not come into question for the approach according to DE 102006053120 A1 since such corrections always make the assumption that the visual axis passes through the spectacle lens at different locations depending on the direction of view, rendering it possible to be able to bring about different optical properties of the spectacles for different directions of view (e.g., in the case of more downwardly directed reading or far vision directed more into the distance). This is not applicable in refractive surgery on the cornea since the cornea of the eye naturally also moves when changing the direction of view as a result of the eye movement. Thus, unlike in the case of a spectacle lens, there is no change in the point where the visual axis passes through the cornea when the eyeball rotates. Consequently, the approach known from DE 102006053120 A1 can only use comparatively simple spectacle lens refractive error correction data as input variables for the control data—with the consequence of correspondingly limited correction options.

DE 10334110 A1 by Carl Zeiss Meditec AG disclosed the production of a cut surface, which at least partly encloses the volume to be separated for the refractive error correction, by virtue of adjusting the focus of the laser radiation along orbits that follow height contours or along a spiral that is oriented on such height contours. Here, the planes in which the height contours are defined, or on the basis of which the spiral is defined, are oriented perpendicular to the principal direction of incidence of the processing laser radiation. What this achieves is that the adjustment of the focus along the optical axis, which is usually implemented by way of an adjustable zoom objective or the like, has the smallest possible effect on the speed of working through the trajectory. Since, as a rule, this adjustment of focus is very much slower than the deflection transversely to the principal direction of incidence of the processing laser radiation, this overall provides a fast production of the cut surface.

This document explains that non-spherical cut surfaces, for example a posterior cut surface in the form of an ellipsoid, are required for refractive error corrections that go beyond a spherical correction, for example also correcting an astigmatism. In this context, DE 10334110 A1 explains that such a cut surface should have a circular outline when viewed in a plan view along the principal direction of incidence of the radiation if the processing laser radiation is deactivated in sections that go beyond such a circular outline. In this case, FIG. 11 shows the conditions present. In so doing, a sectional illustration through a cornea 5 is shown, in which a volume 18 is isolated and prepared for removal. Here, the volume 18 is defined by an anterior cut surface 19 that is produced substantially parallel to the corneal front surface 15 and by a posterior cut surface 20. Thus, (together with the anterior cut surface 19) the posterior cut surface 20 defines, in binding fashion, the curvature which the corneal front side 15 has after the removal of the volume 18. Therefore, it is of particular importance for the optical correction and therefore also referred to as correction surface. The lower part of FIG. 11 shows a plan view 33 of the posterior cut surface 20. FIG. 11 shows a case where an astigmatic correction is intended to be carried out, which is why the correction surface follows an ellipsoid. The upper part of FIG. 11 illustrates two cut lines 20.1 and 20.2 for the cut surface 20, which correspond to the principal axes H1 and H2 of the correction surface. The volume 18 has a circular outline in the plan view 33. Further, the ellipsoid-shaped posterior cut surface 20 is produced by a spiral trajectory 32, along which the position of the focus of the processing laser radiation is adjusted, i.e., on which the centers of the laser beam pulses that bring about the processing effect in the cornea 5 lie. In order to ultimately achieve the circular outline of the posterior cut surface 20, the processing laser radiation is blanked, i.e., modified in such a way that no processing effect occurs there, in regions of the spiral 32 that lie outside of the circular outline. Then, the connection between the posterior cut surface 20 and the anterior cut surface 19 is produced by a circular-conical-frustum-shaped side cut 30. In the plan view 33 of the posterior cut surface 20, this is elucidated by a cross-hatched lenticule edge zone 31, which reaches so far into the cornea of the eye that, overall, the volume 18 is isolated by the anterior cut surface 19, the posterior cut surface 20 and the circular-conical-frustum-shaped or circular cylindrical lenticule edge surface 30.

WO 2010/084162 A2 describes how non-rotationally symmetric correction surfaces are extended to a circular posterior cut surface by use of a transition zone. To this end, the outline of the correction surface lying in a plane is extended by use of the transition region lying in a plane in such a way that, in a plan view, the posterior cut surface forms a rotationally symmetric circle. Here, too, use is made of a circular-conical-frustum-shaped or circular cylindrical edge surface in order to connect the posterior and anterior surface.

Like DE 10334110 A1 or WO 2010/084162 A2, the invention relates to the concept of carrying out a correction of the optical imaging error of the human eye by virtue of a separation of a tissue volume by application of laser radiation being achieved in the cornea of the eye, said tissue volume then being removed from the cornea. As a result, a targeted change in the refractive power of the cornea of the eye is achieved. This change is implemented locally, i.e., in the region of the cornea from which the tissue volume is removed. Usually, the pupil of the eye is used here for orientation purposes. The removal of the separated volume changes the geometry, namely the curvature, of the corneal surface. So that the desired refractive error correction is achieved, the separated volume to be removed must, for these reasons, have specific properties in respect of its form. Following the conventional LASIK method, the separated volume is usually described by three boundaries. An anterior boundary is for example formed at a constant distance below the cornea of the eye. This is particularly simple if the cornea is applanated using a flat contact glass. Since this cut surface lies at the front in the direction, it is referred to as anterior surface or, following the LASIK method known per se, it is referred to as flap or cap cut surface. Further, the volume is delimited by a lower-down surface, which can be referred to as posterior cut surface or, since the volume can be considered to be a lenticule, which can be referred to as a lenticule cut surface. Care is taken that, overall, the volume to be removed changes the curvature of the corneal front surface. As a rule, one of the two surfaces, usually the posterior surface, has a geometry that is decisive for the refractive error correction. In principle, one could consider designing the anterior and the posterior surface in such a way that they have a common cut line. Firstly, this is not possible in the case of a farsightedness correction since the volume to be removed in that case must be thinner in the center, i.e., in the region of the visual axis, than at the edge. Secondly, for operative reasons, a certain minimum thickness of the volume at the edge should be ensured, even in the case of a nearsightedness correction, to allow for a simple removal. Therefore, the anterior surface and the posterior surface are connected by way of a so-called lenticule edge surface, which is also referred to as side cut below. The separated volume is rendered removable by way of these three cut surfaces since the volume is completely surrounded or virtually completely surrounded by the cut surfaces in that case. The absolute position and relative extent of the surfaces in the cornea set the zone within which the optical effect occurs after the removal of the separated volume between these surfaces. As already mentioned, the pupil is used here for orientation purposes. This approach leads to the two cut surfaces, namely the anterior and posterior cut surface, of which one or both can be optically effective, having to be connected to form a closed volume that must have a suitable position within the cornea. Since there are also device-related boundary conditions, for example the possible degrees of freedom of the laser beam deflections, and also application-related boundary conditions, such as, for example, regression effects during the healing process, surgical handling of the tissue volume to be removed, maximum tolerable time duration for producing the cut surfaces, etc., the boundary value problem arising overall is by all means complex.

SUMMARY OF THE INVENTION

The invention is based on designing the definition of the closed volume within the cornea to be as expedient as possible from an application point of view and, in particular, of obtaining a secure and simple enclosure of the volume.

An example embodiment of invention includes a method for producing control data configured to control a laser processing apparatus for refractive error correction of an eye of a patient by surgery, wherein an anterior surface, a posterior surface and a side cut, which are to be produced as cut surfaces in the cornea, are defined for removing a volume in the cornea. The posterior cut surface comprises a non-circular, oval edge, which lies in a plane. The side cut connects the edge with the anterior cut surface and it is embodied as a non-rotationally symmetric cylinder or conical frustum, the base of which forms the edge.

The oval edge lies in a plane. The side cut is embodied as a non-rotationally symmetric cylinder or conical frustum. Its base is the edge. Hence, a directrix of the non-rotationally symmetric cylinder or conical frustum also lies in the plane since the base of the side cut is the non-circular, oval edge of the posterior cut surface.

A further example embodiment of the invention includes an apparatus for producing control data configured to control a laser processing apparatus for refractive error correction of an eye of a patient by surgery, wherein an anterior surface, a posterior surface and a side cut, which are to be produced as cut surfaces in the cornea, are defined for removing a volume in the cornea. The posterior cut surface comprises a non-circular, oval edge, which lies in a plane. The side cut connects the edge with the anterior cut surface and it is embodied as a non-rotationally symmetric cylinder or conical frustum, the base of which forms the edge.

Finally, the object is also achieved by a method for correcting the refractive error of an eye by surgery, in which an anterior cut surface, a posterior cut surface and a side cut, which are produced as cut surfaces in the cornea, are defined for the purposes of removing a volume. The posterior cut surface comprises a non-circular, oval edge, which lies in a plane. The side cut connects the edge to the anterior cut surface. The side cut is embodied as a non-rotationally symmetric cylinder or conical frustum, the base of which is the edge.

The distinction of various surfaces or cut surfaces, which restrict the volume that has to be removed for the refractive error correction, is essential for the understanding of the invention. The volume is bounded by an anterior cut surface which, following the LASIK method known per se, is referred to as anterior cut surface, anterior surface or flap surface or flap cut (or cap surface or cap cut). In the posterior direction, the volume is bounded by a posterior cut surface, posterior surface, lenticule surface or lenticule cut. At least one of these surfaces has an effect on the postoperative curvature of the corneal front side, i.e., on the curvature of the corneal front surface after the removal of the volume. In the description provided here, the assumption is made for reasons of simplicity that only the posterior cut surface is this surface with a corrective effect. However, this should not be construed as a restriction.

The region of the relevant cut surface(s) having a corrective effect is referred to as correction zone in the prior art. By way of example, the correction zone, as described in WO 2010/084162 A2 or in DE 10334110 A1, forms part of the posterior cut surface. Optionally, the entire posterior surface forms the correction zone in the present invention. By way of example, this is the case if astigmatism is also taken into account when correcting the refractive error. On account of the different refractive power along the principal axes of the eye in the case of astigmatism, a non-circular posterior surface of the correction zone is obtained. For that reason, the posterior surface comprises the oval edge. Consequently, in contrast to the prior art, no transition zones by which a connection is created between the edge of the correction zone lying in a plane and the edge of the posterior surface are necessary in one embodiment. In another example embodiment, a non-rotationally symmetric correction zone is extended to a posterior cut surface with an oval edge by use of transition zones. The methods for producing the transition zones, as described in WO 2010/084162 A2, can be used to this end under appropriate modification.

In the present invention, "oval" is understood in the usual mathematical sense, namely as a closed, twice continuously differentiable convex curve lying in a plane. Consequently, the oval edge of the posterior surface comprises no corners, lies in a plane and is always curved in one direction. Naturally, it is a closed curve. An example for a surface with an oval edge is an ovoid surface. Normally, oval also comprises circular; however, this case is excluded for this invention.

The anterior cut surface and the posterior cut surface do not yet circumscribe a closed volume, because the side cut, which connects the edge of the posterior cut surface to the anterior cut surface, is still missing. Since the edge of the posterior surface is oval and directly connected to the side cut, the side cut has a base edge that is formed by the edge of the posterior surface. For the purposes of connecting the posterior cut surface to the anterior cut surface, use is made of the lateral surface of a non-rotationally symmetric body, namely a non-rotationally symmetric cylinder or a non-rotationally symmetric conical frustum, as side cut. As a directrix, the circumferential surface comprises the base edge. Here, the term "directrix" is used within the usual mathematical sense, as is known from, for example, Bronstein I., Taschenbuch der Mathematik, Teubner Verlag, 22nd edition, 1985, Section 2.6.2.4.

The cylinder or conical frustum is for example right, i.e., the height of the cylinder/conical frustum is perpendicular to the plane in which the oval edge lies.

The distance between the base edge and the anterior cut surface, i.e., the height of the cylinder or of the conical frustum, optionally comprises a minimum extent. This is provided so that the volume to be removed has a minimum thickness and a certain amount of stability. In this way, damage to the lenticule to be removed can be avoided, said damage possibly leading to residues in the cornea and consequently influencing the refractive error correction.

In cylindrical jackets, the upper top edge, which lies in the anterior cut surface, has an identical shape as the base edge. The anterior cut surface can extend further than the top edge of the cylinder. In the case of a conical frustum lateral surface, the upper top edge is larger or smaller than the base edge on account of the generatrix that always extends through an apex there, and so the top edge is an identical enlargement or reduction of the base edge. Thus, the top edge has a form that corresponds to the form of the base edge and hence the form of the oval edge of the posterior cut surface.

The anterior cut surface can extend further than the top edge of the cylinder. However, the anterior cut surface for example has a circumference which, in terms of its form, corresponds to the edge of the anterior cut surface. Then, the anterior cut surface has an oval circumference which—projected onto the plane of the edge of the anterior cut surface—corresponds to this edge in terms of its form. In this configuration, the side cut connects the edge of the posterior cut surface directly to the circumference of the anterior cut surface. No cut surfaces that would not take part in bounding the isolating volume occurs in the cornea. In this configuration, the isolated volume, in a plan view on the plane, has an oval outline and neither the posterior nor the anterior cut surface protrudes laterally beyond the outline or the isolating volume. These embodiments are particularly expedient. In the case of a spherical anterior cut surface, the circumference moreover does not lie in one plane. This cut surface is brought to the non-rotationally symmetric, oval circumference by blanking the treated laser radiation.

For a better distinction, the peripheral end of the posterior cut surface is referred to here as "edge"; that of the anterior cut surface is referred to as "circumference" or "circumference line". However, this only serves for distinguishing purposes and should not express a substantive difference.

The side cut has a non-circular base and top edge and coincides with the oval edge of the posterior cut surface on the base edge. Consequently, there is no transition zone in the posterior cut surface in the case of an oval correction zone for converting the oval edge into a circular edge; instead, the side cut adjoins the edge of the correction zone without a gap. Consequently, less volume is removed from the cornea of the eye since the volume under the transition zones, as used in the prior art, need not be removed. Further, guiding the cut is simplified since there is no need to provide transition zones. Only the posterior cut surface is produced using known procedures and, following this, the side cut is introduced into the cornea. Further, the method can be performed quicker by the omission of the transition zone.

Moreover, this avoids allowing the actually produced refractive power change to deviate from the calculated refractive power change as a result of the transition zone. Moreover, the computational outlay for producing the posterior cut surfaces can be reduced since methods for producing the transition zones are omitted. Additionally, the technically complex blanking of laser radiation is no longer necessary.

As mentioned previously, it makes no difference as to whether only one or two surfaces with a corrective effect are used. If only one surface with a corrective effect is used, this is usually the posterior cut surface since, as a rule, this is also produced first. This is not mandatory, however. If use is made of only a single surface with a corrective effect (e.g., the posterior cut surface), the other surface (e.g., the anterior cut surface) must be at a constant distance from the corneal front surface. In the case of two surfaces with a corrective effect, what was said in respect of the design of the surface with a corrective effect naturally applies equally to both surfaces with a corrective effect.

For the purposes of correcting a refractive error that relates to higher-order aberrations than only astigmatism, the posterior surface may have an elliptic edge. On account of the elliptic edge, the side cut has an elliptic directrix for the cylinder or the conical frustum. However, it is also possible to extend a non-rotationally symmetric on non-elliptic correction surface on a posterior cut surface to an elliptic edge. The methods for producing the transition zones, as described in WO 2010/084162 A2, can be used to this end with an appropriate modification.

In order to keep the volume to be removed from the cornea as small as possible, in one example embodiment the side cut to connect the posterior surface to a circumferential line of the anterior surface. If the side cut has the form of a cylinder, then the edge of the posterior cut surface should be selected to be identical to the circumferential line of the anterior cut surface. If a conical frustum is used for the side cut, the surface in the plane delimited by the edge is larger or smaller than the anterior surface, albeit with an identical form.

The configuration of the edge of the posterior cut surface is particularly simple if the plane of the edge is perpendicular to a principal direction of incidence of the laser radiation for producing the cut surfaces. In particular, the plane in which the circumferential line of the anterior cut surface extends is also perpendicular to the principal direction of incidence of the laser radiation. In the case where the side cut is a cylinder, the circumferential surface of the side cut is parallel to the principal direction of incidence.

The methods of all variants for producing the control data can be executed without human interaction. In particular, they can be implemented by a computer that, under control of a program according to the invention, executes the method according to the invention and establishes the control data for the laser device from corresponding prescriptions. The method only prepares a therapy apparatus. In particular, the interaction of a physician is in no way necessary when establishing the control data since no therapeutic intervention is linked to the establishment of the control data at this stage. This only occurs when applying the previously established control data.

To the extent that this description describes methods or individual steps of a method for establishing control data for correcting an optical refractive error, the method or individual steps of the method can be carried out by an appropriately configured apparatus. An analogous statement applies to the explanations of the mode of operation of an apparatus that carries out steps. In this respect, apparatus and method features of this description are equivalent. In particular, it is possible to realize the method using a computer on which a corresponding program according to the invention is implemented.

Here, too, the described features can be combined with one another as desired provided they do not contradict one another from a technical point of view.

The deliberations, developments and advantages that were presented in conjunction with the method for producing control data and the apparatus for producing control data apply analogously in view of the surgical method.

BRIEF DESCRIPTION OF THE DRAWINGS

Below, the invention will be explained in still more detail by way of example, with reference being made to the drawings. In the drawings:

FIG. 1 depicts a schematic illustration of a treatment apparatus or of a treatment appliance for correcting a refractive error, FIG. 3 depicts an illustration of the principle for introducing pulsed laser radiation into the eye during the refractive error correction using the treatment appliance of FIG. 1, FIG. 4 depicts a further schematic illustration of the treatment appliance of FIG. 1, FIG. 5 depicts a schematic sectional illustration through the cornea of the eye with an illustration of a volume to be removed for the purposes of correcting the refractive error, FIG. 6 depicts a section through the cornea of the eye after removing the volume of FIG. 5, FIG. 7 depicts a sectional illustration similar to FIG. 5, FIG. 9 depicts a diagram with possible curves of a refractive power distribution, which is used when establishing the volume to be removed.

DETAILED DESCRIPTION

Figure 2:
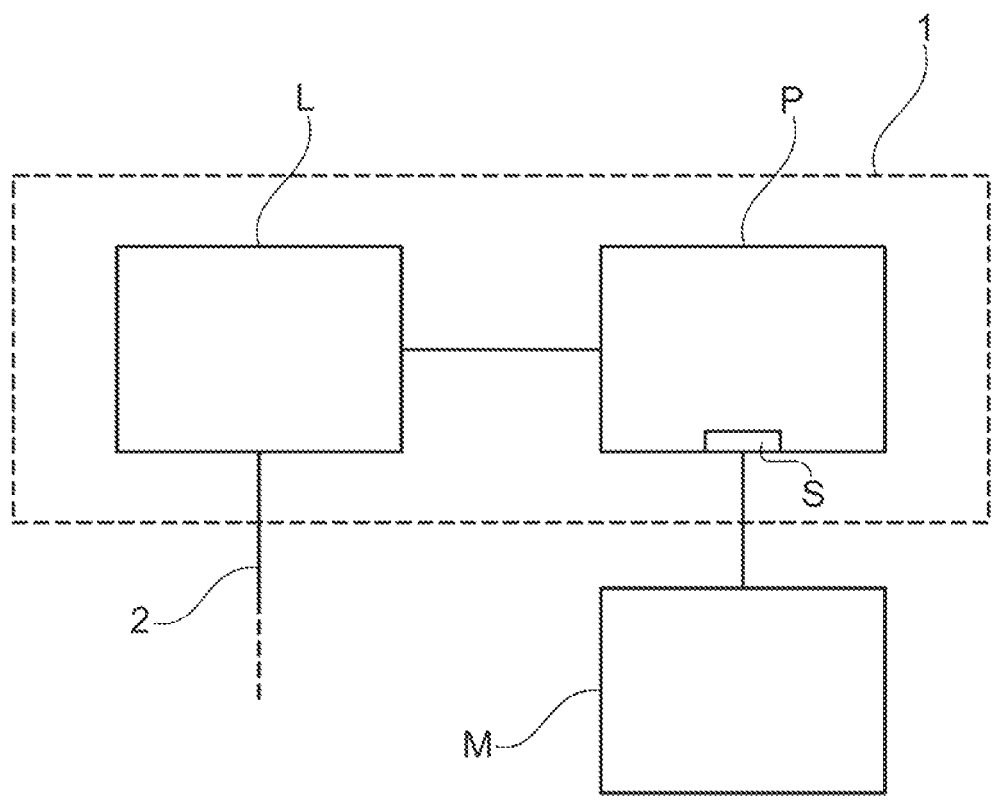
FIG. 2 depicts a schematic illustration in respect of the design of the treatment appliance of FIG. 1.

FIG. 1 depicts a treatment appliance 1 for an ophthalmic surgical method that is similar to the one described in EP 1159986 A1 and U.S. Pat. No. 5,549,632. By application of treatment laser radiation 2, the treatment appliance 1 brings about a refractive error correction on an eye 3 of a patient 4. The refractive error may comprise hyperopia, myopia, presbyopia, astigmatism, mixed astigmatism (astigmatism, in which hyperopia is present in one direction and myopia is present in a direction at right angles thereto), aspherical aberrations and higher-order aberrations. In the described embodiment, the treatment laser radiation 2 is applied as a pulsed laser beam that is focused into the eye 3. Here, the pulse duration lies in the femtosecond range, for example, and the laser radiation 2 acts by way of nonlinear optical effects in the cornea. By way of example, the laser beam comprises laser pulses that are 50 to 800 fs short (for example, 100-400 fs) with a pulse repetition frequency of between 10 and 500 kHz. In the described example embodiment, the components of the appliance 1 are controlled by an integrated control unit, although the latter may also have an independent embodiment.

Before using the treatment appliance, the refractive error of the eye 3 is measured using one or more measuring devices.

FIG. 2 schematically depicts the treatment appliance 1. In this variant, it comprises at least two devices or modules. A laser device L emits the laser beam 2 onto the eye 3. Here, the operation of the laser device L is implemented in fully automated fashion, i.e., the laser device L starts the deflection of the laser beam 2 following an appropriate start signal and produces cut surfaces in the process, said cut surfaces being constructed in the manner yet to be described below and isolating a volume in the cornea of the eye. The control data required for the operation are received by the laser device L in advance as a control data record from a planning device P via control lines not denoted in any more detail. The transmission is implemented prior to the operation of the laser device L. Naturally, communication can also be implemented in wireless fashion. As an alternative to direct communication, it is also possible to arrange the planning unit P in spatially separated fashion from the laser unit L and to provide a corresponding data transmission channel.

In an example embodiment, the control data record is transmitted to the treatment appliance 1 and, in a further example embodiment, an operation of the laser device L is blocked until a valid control data record is present at the laser device L. A valid control data record can be a control data record that, in principle, is suitable for use with the laser device L of the treatment apparatus 1. However, additionally, the validity can also be linked to further tests being passed, for example whether specifications about the treatment appliance 1, e.g., an appliance serial number, or about the patient, e.g., a patient identification number, which are additionally stored in the control data record, correspond to other specifications that, for example, are read at the treatment apparatus or entered separately as soon as the patient is in the correct position for the operation of the laser device L.

The control data record, which is provided to the laser unit L for carrying out the operation, is produced by the planning unit P from measurement data and refractive error data that were established for the eye to be treated. They are supplied to the planning unit P via an interface S and, in the illustrated exemplary embodiment, originate from a measuring device M, which has previously measured the eye of the patient 4. Naturally, the measuring device M can transmit the corresponding measurement data and refractive error data to the planning device P in any suitable way.

The transmission can be implemented by use of memory chips (e.g., by USB or memory stick), magnetic storage units (e.g., disks), by radio (e.g., WLAN, UMTS, Bluetooth) or in wired fashion (e.g., USB, FireWire RS232, CAN bus, Ethernet, etc.). Naturally, the same applies in respect of the data transmission between planning device P and laser device L.

A direct radio or wired link of the measuring device M to the treatment device 1 in respect of the data transmission, which can be used in one variant, is advantageous in that the use of incorrect measurement data and refractive error data can be excluded with the greatest possible reliability. This applies, in particular, if the transfer of the patient from the measuring device M or the measuring devices to the laser device L is implemented by use of the bearing device (not illustrated in the figure), which interacts with the measuring device M and/or with the laser device L in such a way that the respective devices recognize whether the patient 4 is in the respective position for measuring or introducing laser radiation 2. Here, when the patient 4 is moved from the measuring device M to the laser device L, the measurement data and refractive error data can be transferred to the treatment apparatus 1 at the same time.

In an example embodiment, suitable safeguards ensure that the planning device P always produces the control data record belonging to the patient 4 and an erroneous use of an incorrect control data record for a patient 4 is virtually excluded.

The mode of operation of the laser beam 2 is schematically indicated in FIG. 3. Using optics not denoted in any more detail, the treatment laser beam 2 is focused into the cornea 5 of the eye 6. As a result, a focus arises in the cornea 5, said focus covering a spot 6 and having a laser radiation energy density that is so high that, in combination with the pulse length, a nonlinear effect occurs in the eye. By way of example, each pulse of the pulse laser radiation 2 can produce an optical breakthrough in the cornea 5 of the eye at the respective spot 6, said breakthrough, in turn, initiating a plasma bubble as indicated schematically in FIG. 3. As a result, tissue is separated in the cornea 5 by application of this laser pulse. If a plasma bubble arises, the tissue layer separation comprises a larger area than the spot 6, which only covers the focus of the laser radiation 2, even though the conditions for producing the breakthrough are only obtained in the focus. So that an optical breakthrough by each laser pulse is produced by each laser pulse, the energy density, i.e., the fluence of the laser radiation, must lie above a certain, pulse-length-dependent threshold. A person skilled in the art is aware of this relationship, for example from DE 69500997 T2.

Alternatively, a tissue-separating effect by the pulsed laser radiation can also be produced by virtue of a plurality of laser radiation pulses being emitted into a region, with the spots 6 overlapping for a plurality of laser radiation pulses. Then, a plurality of laser radiation pulses interact in order to obtain a tissue-separating effect.

However, the type of tissue separation employed by the treatment appliance 1 has no further relevance for the subsequent description, even though pulsed treatment laser radiation 2 is presented in this description. By way of example, use can be made of a treatment appliance 1 as described in WO 2004/032810 A2. A multiplicity of laser pulse focuses forms a cut surface in the tissue, the form of which depends on the pattern with which the laser pulse focuses are arranged in the tissue. The pattern provides target points for the focal positions at which one or more laser pulse(s) is(are) emitted and defines the form and position of the cut surface.

In order now to carry out the refractive error correction, material is removed out of the region within the cornea 5 by application of the pulsed laser radiation by virtue of tissue layers being separated there, said tissue layers isolating the material and then facilitating a material removal. The removal of material brings about a change in volume in the cornea, which has as a consequence a change in the optical imaging effect of the cornea 5, which is dimensioned precisely in such a way that the previously established refractive error is corrected to the best possible extent. For the purposes of isolating the volume to be removed, the focus of the laser radiation 2 is directed to targets in the cornea 5, as a rule, in a region that lies below the epithelium and Bowman's membrane and above Descemet's membrane and the endothelium. To this end, the treatment appliance 1 comprises a mechanism for adjusting the position of the focus of the laser radiation 2 in the cornea 5. This is shown schematically in FIG. 3.

FIG. 4 only plots elements of the treatment appliance 1 to the extent that these are necessary for understanding the adjustment of the focus. As already mentioned, the laser radiation 2 is focused at a focus 7 in the cornea 5 and the position of the focus 7 in the cornea is adjusted such that, for the purposes of producing cut surfaces, energy of laser radiation pulses, focused at different positions, is introduced into the tissue of the cornea 3. The laser radiation 2 is provided as pulsed radiation by a laser 8. An xy-scanner 9, which is realized in one variant by two substantially orthogonally deflecting galvanometer mirrors, deflects the laser beam coming from the laser 8 in two dimensions such that a deflected laser beam 10 is present downstream of the xy-scanner 9. Consequently, the xy-scanner 9 brings about an adjustment of the position of the focus 7 substantially perpendicular to the principal direction of incidence of the laser radiation 2 into the cornea 5. In addition to the xy-scanner 9, a z-scanner 11 is provided for adjusting the depth position, said z-scanner being embodied as an adjustable telescope, for example. The z-scanner 11 ensures that the z-position of the position of the focus 7, i.e., the position thereof on the optical axis of incidence, is modified. The z-scanner 11 can be disposed upstream or downstream of the xy-scanner 9. The coordinates denoted below by x, y, z therefore relate to the deflection of the position of the focus 7.

The assignment of the individual coordinates to spatial directions is not essential for the functional principle of the treatment appliance 1; however, for the purposes of simpler description, z always denotes the coordinate along the optical axis of incidence of the laser radiation 2 below and x and y denote two mutually orthogonal coordinates in a plane perpendicular to the direction of incidence of the laser beam. Naturally, a person skilled in the art knows that the position of the focus 7 in the cornea 5 can also be described in three dimensions by other coordinate systems; in particular, this need not necessarily be an orthogonal coordinate system. Thus, it is not mandatory for the xy-scanner 9 to deflect about axes that are orthogonal to one another; rather, it is possible to use any scanner that is able to adjust the focus 7 in a plane not containing the axis of incidence of the optical radiation. Consequently, skew coordinate systems are also possible.

Further, it is also possible to use non-Cartesian coordinate systems for describing or controlling the position of the focus 7, as will also still be explained below. Examples of such coordinate systems are spherical coordinates and cylindrical coordinates.

For the purposes of controlling the position of the focus 7, the xy-scanner 9 and the z-scanner 11, which together realize a specific example of a three-dimensional focus adjustment device, are actuated by a controller 12 via lines not denoted in any more detail. The same applies to the laser 8. The controller 3 ensures a suitable synchronized operation of the laser 8 and of the three-dimensional focus adjustment device, realized in exemplary fashion by the xy-scanner 9 and the z-scanner 11, and so the position of the focus 7 in the cornea 5 is adjusted in such a way that, ultimately, a material of a certain volume is isolated, with the subsequent volume removal bringing about a desired refractive error correction.

The controller 12 operates according to predetermined control data, which predetermine the target points for the focal adjustment. As a rule, the control data are combined in a control data record. In one embodiment, the latter predetermines the coordinates of the target points as a pattern, wherein the sequence of the target points in the control data record sets the stringing together of the focal positions and hence, consequently, a trajectory (also referred to as path here). In one embodiment, the control data record contains the target points as specific manipulated variables for the focal position adjustment mechanism, e.g., for the xy-scanner 9 and the z-scanner 11. For the purposes of preparing the ophthalmic surgical method, i.e., before the actual operation method can be carried out, the target points and for example also the sequence thereof in the pattern are determined. The surgical intervention must be planned in advance to the effect of establishing control data for the treatment appliance 1, the application of which then obtains an optimal refractive error correction for the patient 4.

The initial goal is to set the volume to be isolated in the cornea 5 and to be removed subsequently. As already explained on the basis of FIG. 2, this needs determination of the correction requirements.

In respect of the nomenclature used in this description, it should be noted that the attachment of an asterisk to variables clarifies that this relates to variables that are obtained after a correction. Under the justified assumption that a change in thickness of the cornea 5 substantially modifies the radius of curvature of the corneal front side 15 that faces the air but does not modify the radius of curvature of the corneal back side 16 that faces the interior of the eye, the radius of curvature $R_{CV}$ of the corneal front side 15 is modified by removing the volume. The cornea 5 that is reduced by the volume and that has a modified corneal surface 15* has a correspondingly modified imaging effect on account of the modified front side curvature, and so a corrected focus lies on the retina 14.

Therefore, the curvature $R^*_{CV}$ of the modified corneal front surface 15* to be achieved is established for determining the pattern of the target points.

Now, using the value $B_{COR}$, the curvature of the modified corneal front surface 15* is set as follows:

$$R_{CV}^*(r,\varphi)=1/((1/R_{CV}(r,\varphi))+B_{COR}(r,\varphi)/(n_c-1))+F \qquad (1)$$

In equation (1), $n_c$ denotes the refractive power of the material of the cornea. The corresponding value usually lies at 1.376; $B_{COR}$ denotes the refractive power change that is required to correct the refractive error. $B_{COR}$ has a radial dependence. Here, radial dependence is understood to mean that there are two values r1 and r2 for the radius r, for which the refractive power change has different values at all angles $\varphi$.

Examples of possible curves of the refractive power change are shown in exemplary fashion in FIG. 9, which shows the function $B_{COR}$ in different exemplary curves Ka to Ke as a function of the radius r.

Ka is a conventional refractive index of spectacles according to the prior art as per DE 102006053120 A1, albeit already related to the plane of the corneal vertex in the illustration of FIG. 9. However, there is no prompt for this relationship in the specified prior art. It was only plotted here for a better comparability with the exemplary curves Kb to Ke according to the invention. The curve Kb is constant up to a radius lying beyond a radius $r_s$ and then it drops off. Here, the radius $r_s$ is the scotopic pupil radius, i.e., the pupil radius that sets in in the case of scotopic vision. The refractive power change according to curve Kc is piecewise constant up to the value $r_s$, with a jump from a higher value to a lower value being implemented below a radius $r_p$, which corresponds to the photopic pupil radius. Such a variation in the refractive power correction over the pupil cross section is particularly advantageous in the case of presbyopia. In that case, seeing in the near region usually occurs in the case of good illumination, for example when reading. Then, as a rule, the pupil has narrowed to the photopic pupil radius on account of the good illumination. The refractive power correction value required in that case represents an optimal adaptation to near vision, e.g., an optimal viewing distance of approximately 25 to 70 cm. For the other extreme case, namely scotopic vision, which is usually linked to looking into the distance (e.g., in the case of driving at night), the pupil, by contrast, is opened to the maximum possible extent. Then, regions of the pupil that have a different (e.g., lower) value for the refractive power correction also contribute during optical imaging. During optical perception, the human brain is able to correct an image afflicted by optical aberrations in this way (different focal position for the center of the pupil and edge regions of the pupil). The refractive power correction curves shown in the curves Kc or Kd thus allow an increase in the depth of field range by deliberately accepting an imaging aberration since the imaging aberration is compensated by the brain.

Then the refractive power correction drops further beyond the pupil radius $r_s$. The non-discontinuous drop in the refractive power correction to the value of zero is advantageous from an anatomical point of view. It allows matching of the corrected corneal front side radius, which sets in on account of the correction, to the original corneal radius of curvature, i.e., the preoperative radius, at the edge of the corrected region, i.e., at the edge of the volume to be removed. In relation to the illustration of FIG. 5, this means that, in the edge region of the volume to be removed, at which the radii $R_F$ and $R_L$ coincide in the illustration of FIG. 5, matching of these radii is implemented. As a result, after the correction, the transition from the new corneal front side radius $R^*_{CV}$, which is present in the region in which the volume 18 was removed, is comparable to the original corneal radius of curvature $R_{CV}$ at the corneal front surface. As a result, the optical correction overall is better, which is only obtainable by the radially varying refractive power correction.

The drop of the refractive power correction to the value of zero is for example implemented in a region outside of the dark-adapted pupil radius, i.e., in a region of the cornea of the eye that has no further relevance for vision.

A similar profile is shown by the curve Kd; however, there is a smooth transition in this case from the first value of the refractive power change below $r_p$ to the second value present at $r_s$. Moreover, the first value is lower here in an exemplary fashion than the second value. Naturally, this can also be used in this way for the curve Kc, depending on the desired correction requirements. Curve Ke shows a smooth profile that continuously decreases.

The locally dependent refractive power changes with a radial dependence, explained on the basis of FIG. 9, are examples of the refractive power change that is used when determining the volume to be removed in the operation.

The factor F expresses the optical effect of the change in thickness which is experienced by the cornea as a result of the surgical intervention and, to a first approximation, it can be considered to be a constant factor which, for example, can be determined in advance by experiment. For a highly accurate correction, the factor can be calculated according to the following equation:

$$F=(1-1/n_c)\cdot\Delta z(r=0,\varphi) \qquad (2)$$

Here, $\Delta z(r=0, \varphi)$ is the central thickness of the volume to be removed.

For an accurate determination, $R_{CV}^*$ is calculated iteratively by virtue of the variable $\Delta z(r=0,\varphi)$ being deduced in the i-th calculation from the difference $1/R_{CV}^*(r=0,\varphi)-1/R_{CV}(r=0,\varphi)$ and the corresponding result obtained therefrom being applied to the change in thickness in the (i+1)-th calculation of $R^*_{CV}$. This can be carried out until a termination criterion is satisfied, for example if the difference of the result for the change in thickness in two successive iterations steps lies below an accordingly set limit. By way of example, this limit can be set by way of a constant difference that corresponds to an accuracy of the refractive correction that is appropriate for the treatment.

Figure 10:
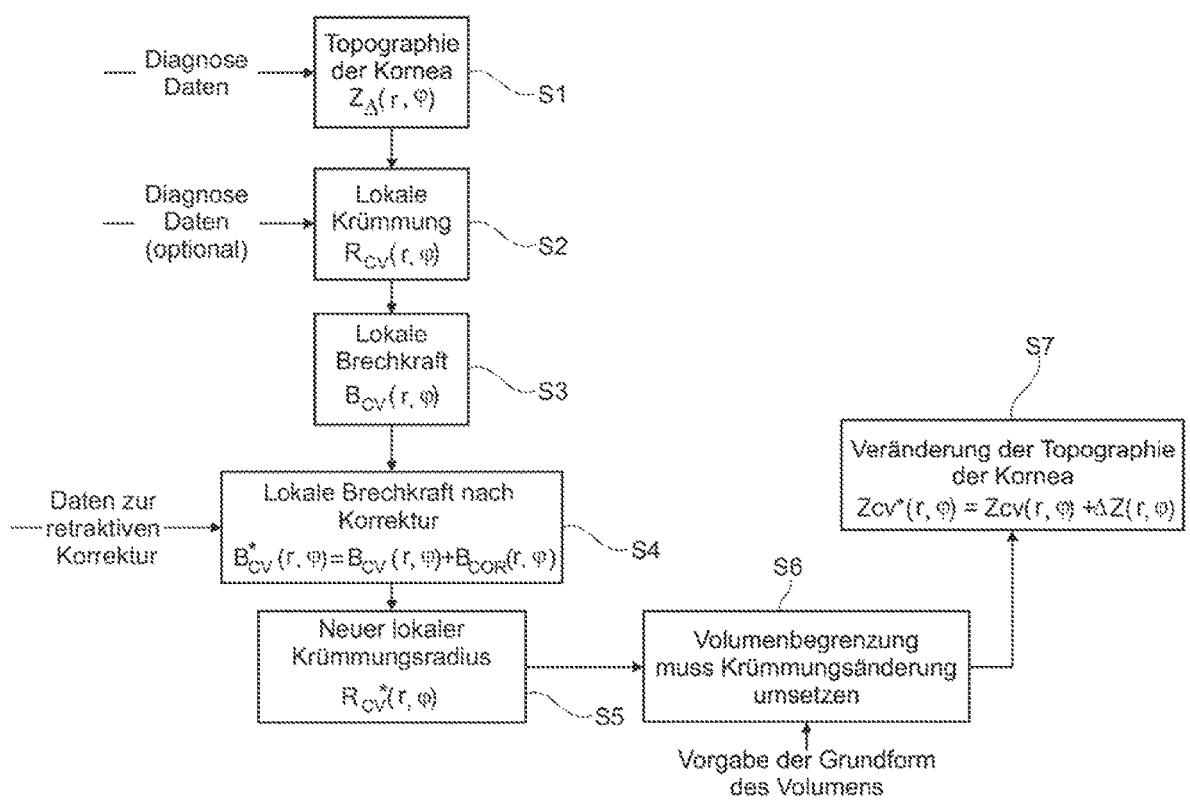
FIG. 10 depicts a flowchart for establishing the volume to be removed.

In general, the method illustrated in FIG. 10 can be carried out in the process. The topography of the cornea is calculated from diagnostic data, as already mentioned at the outset in the general part of the description, in a step S1. The radial curvature profile of the corneal front side 15 is established from this topography. Rather than using the topography data from step S1, this can also be established directly from diagnostic data such that step S2 either follows step S1 or diagnostic data are used directly, as indicated in FIG. 10 by the appended "(optional)". Thus, step S1 is optional.

The local refractive power of the cornea is established in a step S3.

In a step S4, the required local refractive power change $B_{COR}$ is determined from the data of the desired refractive correction and the local refractive power desired after the correction is determined from the local refractive power using said local refractive power change.

The new local radius of curvature $R^*_{CV}(r, \varphi)$ emerges therefrom in step S5. Instead of calculating the local refractive power $B_{CV}$ in step S3, calculations can also be carried out directly using the local curvature $R_{CV}$ from step S2 if equation (1) above is used. Here, quite fundamentally, reference should be made to the fact that refractive power and radius of curvature can be converted into one another using a simple equation. The following holds true: $B=(n_C-1)/R$, where B is the refractive power and R is the radius assigned to this refractive power. Thus, within the scope of the invention, it is possible to switch between the consideration or representation of the radius and the refractive power at all times. The equation to be used when establishing the control data in the case of refractive power representations is:

$$B^*_{CV}(r, \varphi) = \frac{1}{\frac{1}{B_{CV}(r, \varphi) + B_{COR}(r, \varphi)} + \frac{F}{(n_C - 1)}}$$

To the extent that reference is made here to the radius of the corneal front surface, use can also be made, quite analogously, of the refractive power, and so all explanations provided here in conjunction with the radius of the corneal front surface naturally also apply analogously to the refractive power representation or perspective if R is replaced by B according to the aforementioned relationship.

For the volume whose removal brings about the aforementioned change of curvature of the corneal front surface 15, the boundary surface isolating the volume is now set in a step S6. Here, the intended basic form of the volume should be taken into account.

In a first variant, a free-form surface that circumscribes the volume whose removal brings about the change in curvature is defined by application of numerical methods known to a person skilled in the art. To this end, the volume thickness required for the desired modification of curvature is established along the z-axis. From this, the volume emerges as a function of r, $\varphi$ (in cylindrical coordinates) and, in turn, the boundary surface emerges therefrom.

By contrast, an analytical calculation supplies the following variant, already mentioned in DE 102006053120 A1, in which the boundary surface of the volume is substantially constructed by two partial surfaces, and an anterior partial surface lying toward the corneal surface 15 and an opposing posterior partial surface. The corresponding relationships are shown in FIG. 5. Toward the corneal front surface 15, the volume 18 is delimited by an anterior cut surface 19, which lies at a constant distance $d_F$ below the corneal front surface 15. In a manner analogous to laser keratomes, this anterior cut surface 19 is also referred to as anterior cut surface 19 since, in that case, it serves, in combination with an opening cut to the edge of the cornea 5 of the eye, to be able to lift a lamella in the form of a "flap" from the cornea 5 lying therebelow. Naturally, this type of removal of the previously isolated volume 18 is also possible in this case.

The anterior cut surface 19 is for example spherical since a radius of curvature can then be specified therefor, said radius of curvature being less than the radius of curvature $R_{CV}$ by the lamella thickness $d_F$.

In the posterior direction, the volume 18 that should be removed from the cornea 5 is delimited by a posterior cut surface 20 which already cannot be at a constant distance from the corneal front surface 15 as a matter of principle because otherwise virtually no corrective effect would occur. Therefore, the posterior cut surface 20 is embodied in such a way that the volume 18 is present in the form of a lenticule, which is why the posterior cut surface 20 is also referred to as lenticule surface. In FIG. 5, it is likewise plotted as a spherical surface with a radius of curvature $R_L$ in exemplary fashion, with, naturally, the center of this curvature not coinciding with the center of curvature of the corneal front surface 15, which is likewise spherical in FIG. 5. At the edge, the two surfaces 19, 20 are for example connected by a lenticule edge surface, which is referred to as side cut 30 below, in order to completely surround the volume to be removed and, at the same time, ensure a minimum thickness at the edge.

FIG. 6 shows the relationships after the removal of the volume 18. The radius of the modified corneal front surface 15* now is $R_{CV}^*$ and, for example, can be calculated using the above-described equations. Here, the thickness $d_L=\Delta z(r=0, \varphi)$ of the removed volume 18 is decisive for the change in radius, as elucidated by FIG. 7. In this figure, the posterior cut surface is spherical in simplified terms. Consequently, the height $h_F$ of the spherical cap defined by the anterior cut surface 19, the height $h_L$ of the spherical cap defined by the posterior cut surface 20 and the thickness & of the volume 18 to be removed are also plotted as further variables.

On account of the constant distance between the corneal front surface 15 and anterior cut surface 19, the posterior cut surface 20 sets the curvature profile of the corneal front surface 15* after the removal of the volume 18.

If the factor F should be taken into account during the calculation, the change in the topography of the cornea is also taken into account in step S7, i.e., the current central thickness is calculated. With the value for the factor F emerging therefrom, steps S4 to S6 or S5 to S6 can be run through again or can be run through multiple times in the form of an iteration.

The embodiment of the volume 18 delimited by an anterior cut surface 19 with a constant distance from the corneal front surface 15 and a posterior cut surface 20, as shown in the figures, is only one variant for delimiting the volume 18. However, it is advantageous in that the optical correction is substantially only set by one surface (the posterior cut surface 20), and so the analytical description of the other partial surface of the boundary surface is simple.

Furthermore, optimal safety margins in respect of the distance of the volume from the corneal front surface 15 and corneal back surface 16 are provided. The residual thickness $d_F$ between the anterior cut surface 19 and the corneal front surface 15 can be set to be constant at a value of 50 to 200 µm, for example. In particular, it can be chosen in such a way that the pain-sensitive epithelium remains in the lamella, the latter being formed by the anterior cut surface 19 under the corneal front surface 15. Also, the embodiment of the spherical anterior cut surface 19 has continuity with previous keratometer cuts, which is advantageous for the acceptance of the method.

Figure 8:
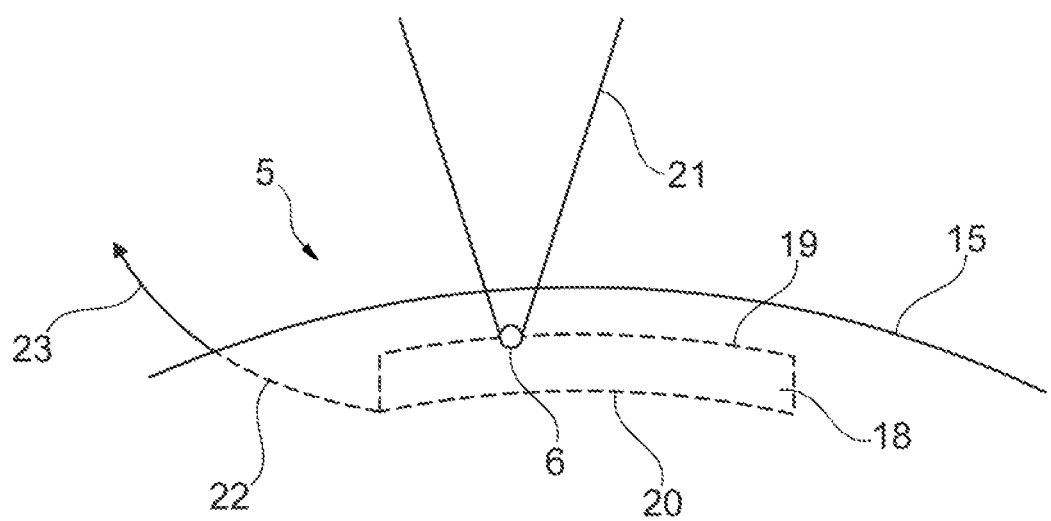
FIG. 8 depicts a schematic sectional illustration through the cornea of the eye for elucidating the removal of the volume.

After the cut surfaces 19 and 20 are produced, the volume 18 isolated thus is then removed from the cornea 5. This is illustrated schematically in FIG. 8, which moreover elucidates that the cut surfaces 19 and 20 are produced by the action of the treatment laser beam incident in a focal cone 21, for example by stringing together plasma bubbles such that, in an example embodiment, the anterior cut surface 19 and the posterior cut surface 20 are produced by suitable three-dimensional adjustment of the focal position of the pulse laser radiation 2.

The features described above and below are also possible in these variants, particularly in relation to determining the boundary surface, the geometric definition thereof and the establishment of control parameters.

If both the posterior cut surface 20 and the anterior cut surface 19 are produced by application of pulsed laser radiation, it is expedient to form the posterior cut surface 20 before the anterior cut surface 19 since the optical result in the posterior cut surface 20 can be achieved better (or even only be achieved at all) if there has not yet been a change in the cornea 5 above the posterior cut surface 20.

Figure 12:
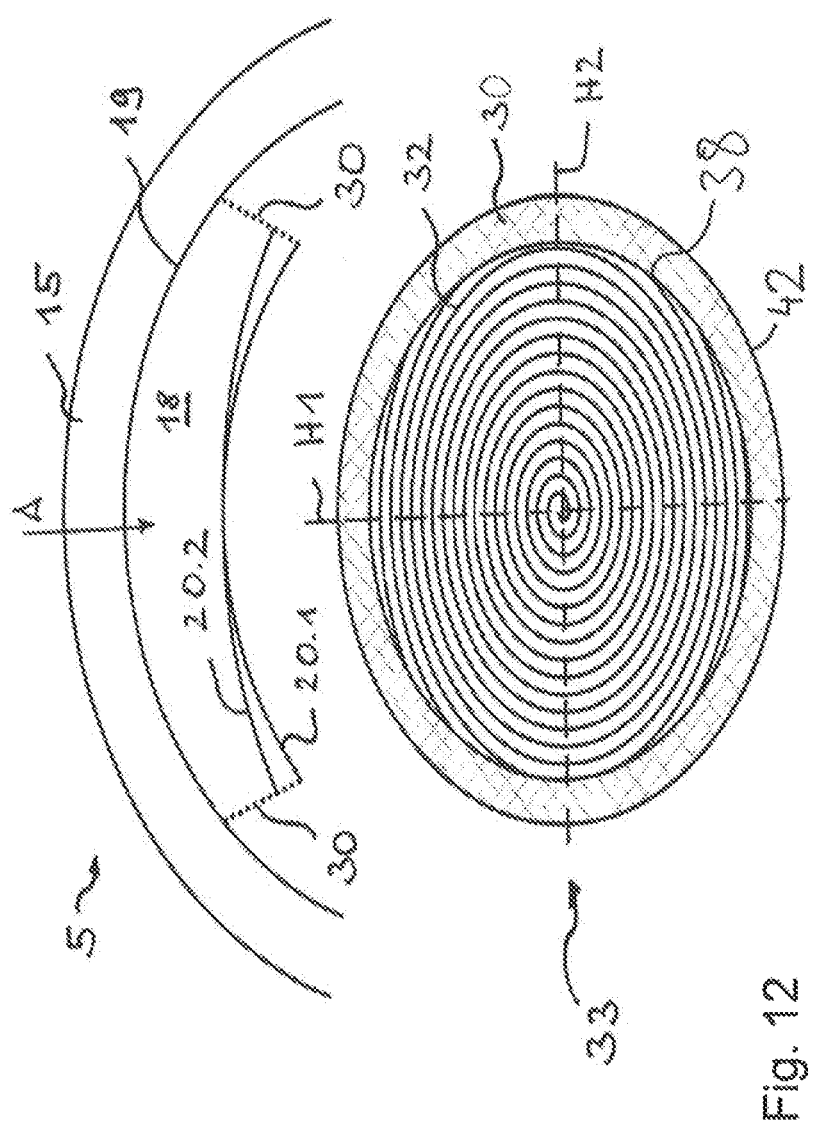
FIG. 12 depicts a sectional illustration through the cornea of the eye for elucidating an anterior and a posterior cut surface in combination with a plan view of the posterior cut surface, wherein a conical frustum lateral surface is provided as a cut surface.

FIG. 12 shows an illustration which, in its upper part, corresponds in terms of style to the view of FIG. 5. The lower part shows a plan view 33 of the posterior cut surface 20 and the side cut 30, which is elucidated in the sectional illustration lying thereabove by a cut line 20.1.

For the purposes of isolating the volume 18, both the anterior cut surface 19 and the posterior cut surface 20 are produced in the cornea 5 of the eye in the manner described above. In the process, a correction surface is produced which, in a plan view, is non-circular and oval—elliptical in this case for the purposes of correcting an astigmatism. As the plan view 33 on the posterior cut surface 20 shows, this correction surface is produced by a spiral 32 which, for example, runs from the interior of the correction surface to the outside. The spiral 32 defines a trajectory for adjusting the position of the laser beam focus. Here, the center of the spiral 32 for example (but not necessarily) lies at the highest point of the correction surface. The spiral 32 is based on height contours, as a result of which the z-position (position along the principal direction of incidence A of the laser radiation) of the focal position is adjusted continuously. Instead of a group of closed scan lines that never intersect, a continuous scan line is present. Local spatially dependent refractive power corrections $B(r, \varphi)$ can easily be represented and produced by the modulation of the angle-dependent radial function $r(\varphi)$ by way of a spiral 32 that is radially "deformed" in this way.

Figure 11:
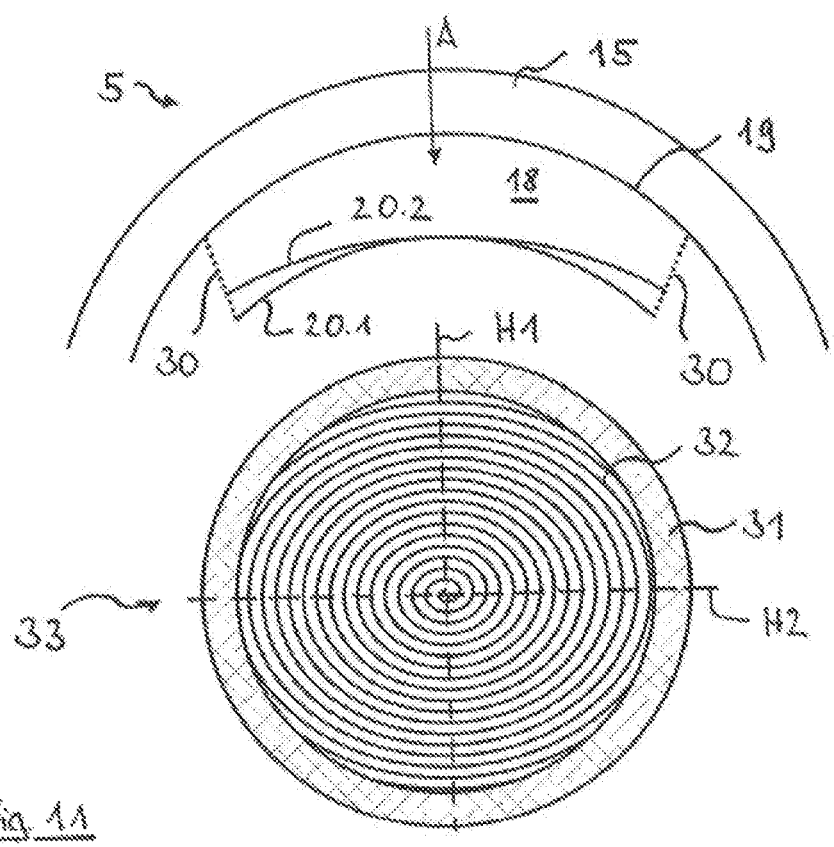
FIG. 11 depicts a sectional illustration through the cornea of the eye for elucidating an anterior and a posterior cut surface in combination with a plan view of the posterior cut surface, wherein the cut surface designs correspond to the prior art.

In contrast to the prior art according to FIG. 11, a circumference of the correction surface simultaneously forms an edge 38 of the posterior cut surface 20. For the edge 38 $r_{MAX'}$ ($f_P$, $\varphi$) of the posterior cut surface 20, z=constant applies; thus, it lies in an xy-plane 40. The correction surface that is required for the optical correction consequently extends over the complete posterior cut surface 20. Here, the trajectory 32 is illustrated using a full line. Just like the edge of the correction surface, the edge 38 of the posterior cut surface 20 is non-circular and oval, in particular elliptical. FIG. 12 plots, in exemplary fashion, an elliptic posterior cut surface 20, which has principal axes H1 and H2. In exemplary fashion, the cut lines 20.1 and 20.2 show the curvature profile of these principal axes. The intersection points of the principal axes H1 and H2 with the edge 38 lie in the plane 40, like the entire edge 38. Hence, there is no need to provide a lenticule edge zone 31 like in the prior art according to FIG. 11.

In FIG. 12, the sectional illustration shows that the edge 38 of the posterior cut surface 20 lies in the plane 40 that is perpendicular to the principal direction of incidence A. The connection between the posterior cut surface 20 and the anterior cut surface 19 is produced using a side cut 30, shown in FIG. 12, that has the shape of the lateral surface of a cone. The edge 38 of the posterior cut surface 20 is the base of the conical frustum, the lateral surface of which forms the side cut 30. Consequently, the directrix, and hence the base edge of the conical frustum for the side cut 30, is non-circular and oval, in particular elliptical. A top edge 42 of the lateral surface of the conical frustum follows in terms of its profile the non-circular oval profile of the base surface of the posterior cut surface 20. In FIG. 12, the side cut 30 is illustrated using hatching.

Figure 13:
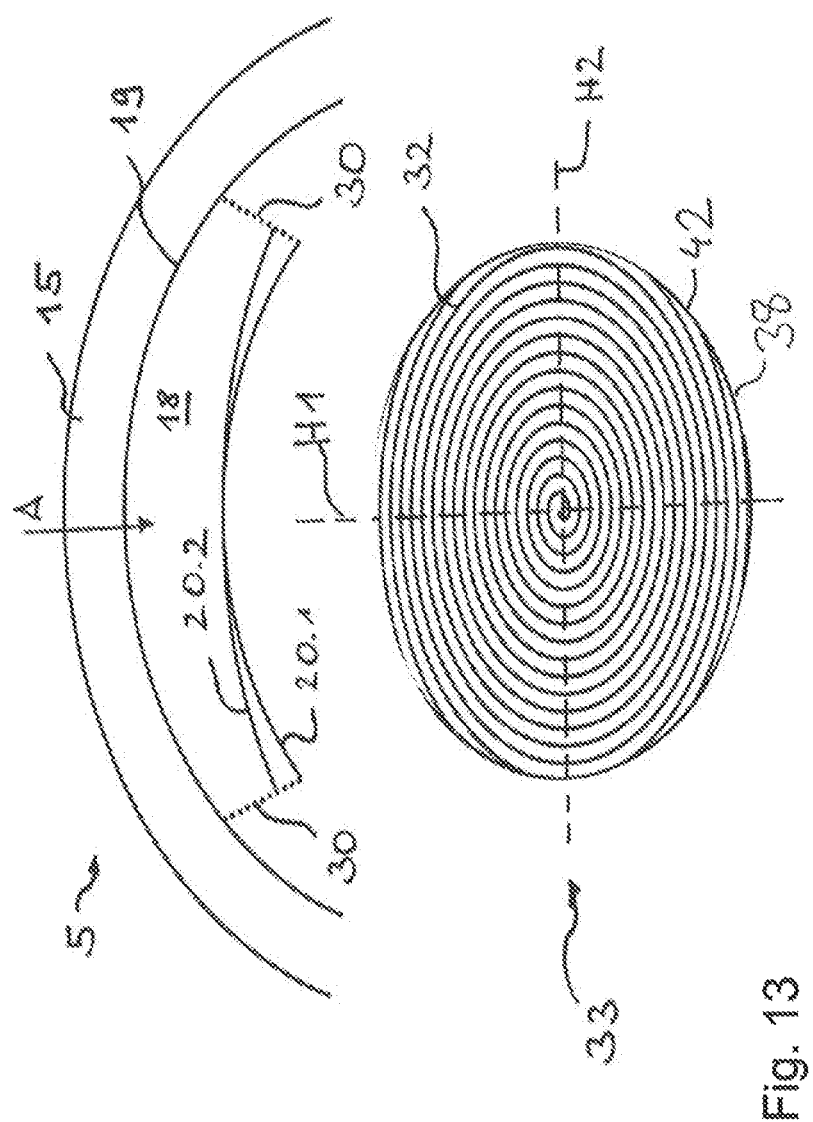
FIG. 13 depicts a sectional illustration through the cornea of the eye for elucidating an anterior and a posterior cut surface in combination with a plan view of the posterior cut surface, wherein a lateral cylinder surface is provided as a cut surface.

In the embodiment of FIG. 13, the side cut is embodied as a lateral surface of a cylinder and not as a lateral surface of a conical frustum. Therefore, it is not plotted in the plan view 33 of FIG. 13. The side cut 30 connects the oval edge 38 of the posterior cut surface 20 to the circumference of the anterior cut surface 19, which has the same form. On account of the conical-frustum-like embodiment of the side cut 30, the circumference has the same form as the oval edge 38—i.e., it is identical apart from an enlargement or reduction.

The embodiments of FIGS. 12 and 13 substantially differ in two aspects. Firstly, the side cut 30 is not conical-frustum-shaped in FIG. 13. Secondly, the anterior cut surface 19 in FIG. 12 is not matched in terms of its circumference to, but larger than, the top edge 42. This is a simplified embodiment. Designing the top edge 42 and the circumference of the posterior cut surface 19 to be identical may be helpful as this ensures that all produced cuts also delimit the volume 18 and that there are no cut regions that are not involved in the delimitation. Therefore, a corresponding circumference of the anterior cut surface 19, which corresponds to the form of the edge 38, may be utilized for all embodiments. The side views of FIGS. 14 and 15 also show this embodiment.

Figure 14:
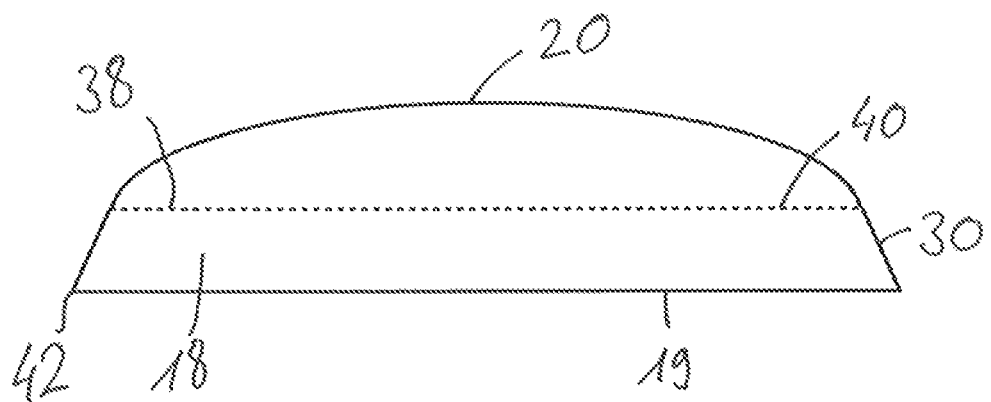
FIG. 14 is a sectional illustration of the volume of FIG. 12 to be removed, along a principal axis H2.

The volume 18 assembled from the posterior cut surface 20, the anterior cut surface 19 and the side cut 30 is identifiable in the cross section in FIG. 14. From this, it is also clear that the oval edge 38, and hence the directrix of the lateral surface of the conical frustum, lies in the plane 40. In particular, it is also clear that that the side cut 30 is incident on the circumference of the anterior cut surface 19, and so the top edge 42 and outline of the anterior cut surface coincide. Then, the circumference of the anterior cut surface 19 has the form of the edge 38 of the posterior cut surface 20. However, this is optional; the anterior cut surface 19 can also be larger than the base surface of the conical frustum in the anterior cut surface 19 or it can be rotationally symmetric. In a first variant, the volume 18 has an oval, in particular elliptical, outline in a plan view.

Figure 15:
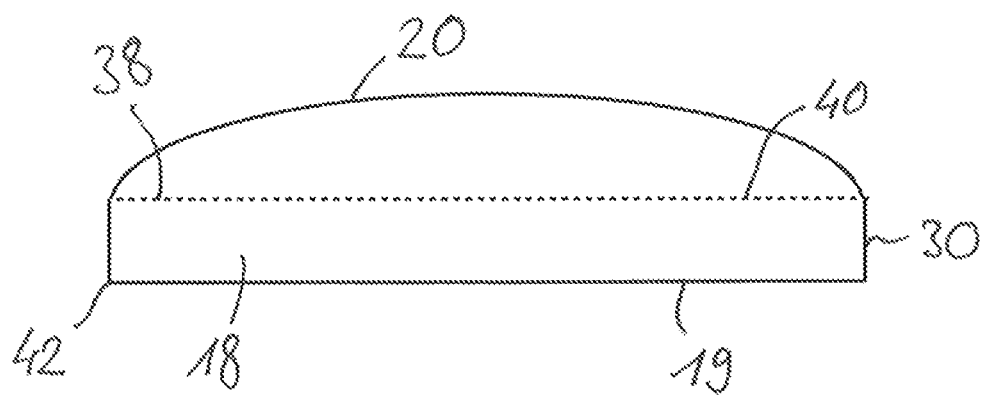
FIG. 15 is a sectional illustration of the volume of FIG. 13 to be removed, along the principal axis H2.
Figure 16:
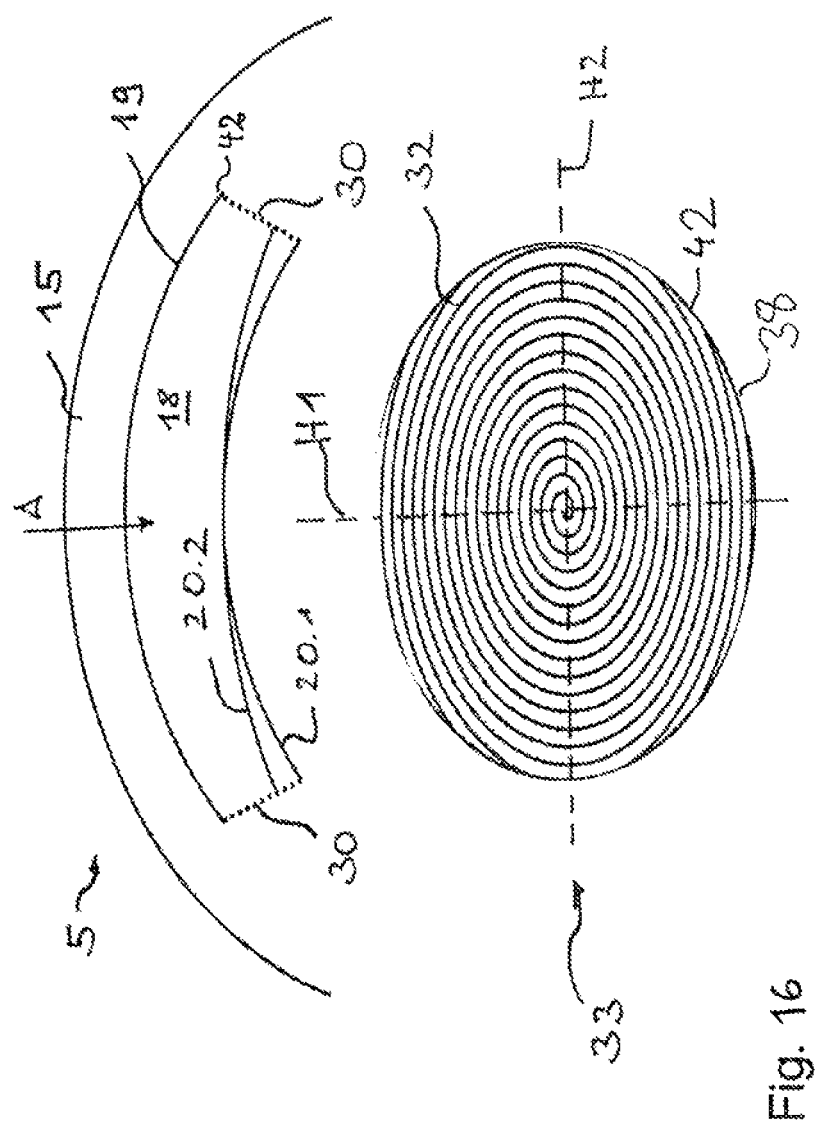
FIG. 16 depicts a sectional illustration, similar to FIG. 14, in which the anterior cut surface has a circumference that corresponds in terms of its form to the edge of the posterior cut surface.
Figure 17:
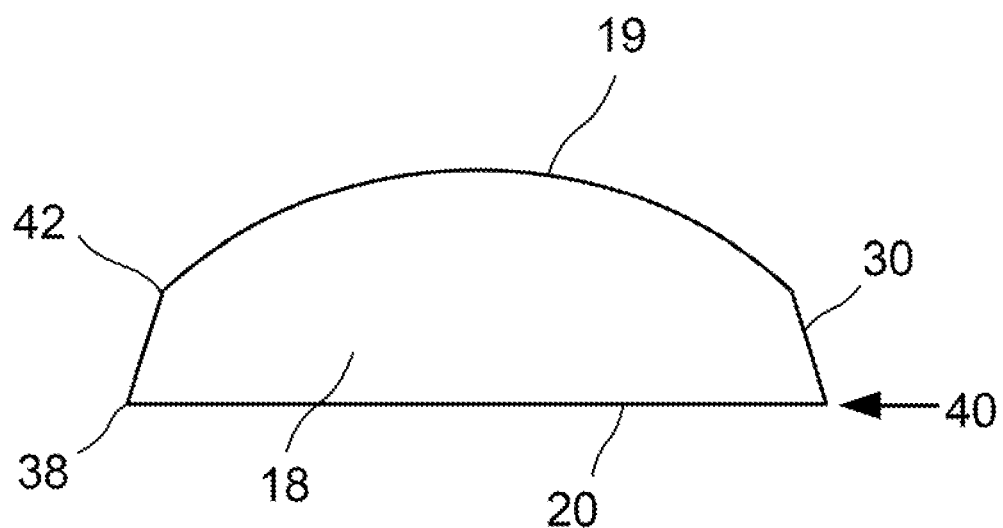
FIGS. 17 and 18 depict sectional illustrations similar to FIGS. 15 and 15 for an anterior cut surface.
Figure 18:
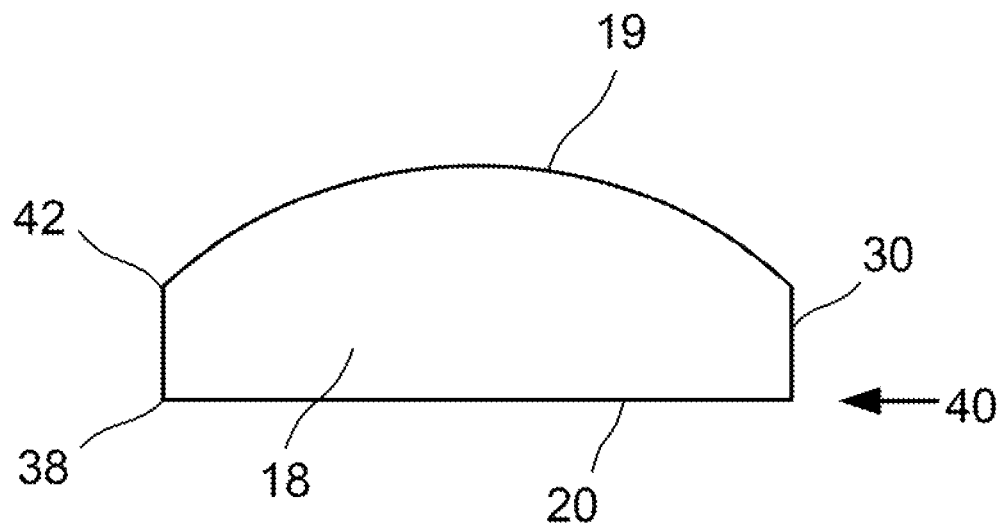

Optionally, the posterior cut surface 20 is an ellipse, which can be described by the principal axes H1 and H2. If the anterior cut surface 19 comprises a circumferential line that coincides with the top edge 42 of the side cut 30, the anterior cut surface 19 can be described by the same principal axes H1 and H2. This is shown in FIGS. 14 and 15 and applies if they the anterior cut surface 19 is not spherically curved. In other embodiments, illustrated in FIGS. 16 to 18, the anterior cut surface 19 is spherically curved but nevertheless has a circumferential line that, in terms of its form, corresponds to the edge 38 of the posterior cut surface 20 and the side cut 30 directly connects the edge 38 of the posterior cut surface 20 to the circumferential line of the anterior cut surface 19. Then, the circumferential line of the anterior cut surface 20 does not lie in a plane. Naturally, this is possible with a side cut 30 that is cylindrical or has the shape of a lateral surface of a cone.

In all embodiments in which the side cut 30 directly connects the edge 38 of the posterior cut surface 20 to the circumferential line of the anterior cut surface 19, none of the cut surfaces protrudes laterally beyond the oval volume 18 in the plan view and all cut surfaces are involved in delimiting the oval volume 19 over their entire extent.

The embodiment of the volume 18 to be removed shown in FIGS. 13 and 15 differs from the embodiment shown in FIGS. 12 and 14 by virtue of the side cut 30 being embodied as a lateral surface of a cylinder and not as a lateral surface of a conical frustum. In both embodiments, the plane 42 is perpendicular to the principal direction of incidence of the laser radiation.

The use of pulsed laser radiation is not the only way in which the surgical refraction correction can be carried out. Rather, the determination of control data for operating the apparatus described here can be used in virtually any surgical method in which a volume is removed from the cornea 5 of the eye by application of an apparatus under the control of control data or added thereto, as already explained in the general part of the description.

All statements in relation to curvatures of the cut surfaces relate to the state of the material to be treated at the time of introducing the laser beam. In the case of the cornea of the eye, this may be a state in which the cornea is deformed by a contact glass, for example into a spherically curved or planar corneal front side.

The invention claimed is:

1. A method for refractive error correction of an eye by surgery, the refractive error including astigmatism and the method comprising:
    applying laser radiation to enclose a volume in the cornea, the volume being bounded by an anterior surface of the volume defined by at least part of an anterior cut surface, a posterior surface of the volume defined by a posterior cut surface and an edge surface of the volume defined by a side cut in the cornea;
    the method further comprising:
    creating the posterior cut surface to comprise a non-circular, oval edge, wherein the non-circular, oval edge lies in a plane;
    creating the side cut that connects the non-circular, oval edge of the posterior cut surface to the anterior cut surface;
    creating the side cut as a lateral surface of a non-rotationally symmetric cylinder or conical frustum, the directrix of which is the non-circular oval edge; and
    creating the side cut such that the lateral surface meets the anterior cut surface at a circumference of the anterior surface to define a circumferential closed curve circumscribing the anterior surface of the volume and wherein the circumferential closed curve does not lie in a plane.

2. The method as claimed in claim 1, further comprising creating the posterior cut surface to comprise an elliptical edge.

3. The method as claimed in claim 1, further comprising creating the anterior surface to include a perimeter which, corresponds to the circumference and creating the side cut to connect the posterior cut surface to the perimeter of the anterior cut surface.

4. The method as claimed in claim 3, further comprising creating the anterior cut surface to be spherically curved and creating the circumference to not lie in a plane.

5. The method as claimed in claim 3, further comprising creating the anterior cut surface to comprise an elliptical circumference.

6. The method as claimed in claim 1, further comprising creating the isolated volume to have an oval outline in a plan view on the plane and to have neither of the anterior cut surface and the posterior cut surface project laterally beyond the outline or the isolated volume.

7. The method as claimed in claim 1, further comprising creating the plane of the non-circular, oval edge to be perpendicular to a principal direction of incidence of laser radiation that is used to produce the anterior cut surface and the posterior cut surface.

* * * * *

UNITED STATES PATENT AND TRADEMARK OFFICE
CERTIFICATE OF CORRECTION

| | | |
|---|---|---|
| PATENT NO. | : 11,272,986 B2 | Page 1 of 1 |
| APPLICATION NO. | : 16/322352 | |
| DATED | : March 15, 2022 | |
| INVENTOR(S) | : Dishler et al. | |

It is certified that error appears in the above-identified patent and that said Letters Patent is hereby corrected as shown below:

On the Title Page

(56) Reference Cited; U.S. Patent Document delete "56,556,186" and insert --5,656,186--

In the Specification

Column 16, Line 58 delete "thickness & of" and insert --thickness $d_L$--

Signed and Sealed this
Twenty-fifth Day of October, 2022

*Katherine Kelly Vidal*

Katherine Kelly Vidal
*Director of the United States Patent and Trademark Office*